United States Patent [19]

Green et al.

[11] Patent Number: 5,314,435
[45] Date of Patent: May 24, 1994

[54] ANVIL DELIVERY SYSTEM

[75] Inventors: David Green, Westport; Henry Bolanos, East Norwalk, both of Conn.; Patrick F. Leahy, Dublin, Israel

[73] Assignee: United States Surgical Corporation, Norwalk, Conn.

[21] Appl. No.: 886,040

[22] Filed: May 19, 1992

[51] Int. Cl.⁵ ............................................. A61B 17/00
[52] U.S. Cl. .................................. 606/153; 606/1; 227/175
[58] Field of Search ............... 227/175, 178, 179, 181, 227/19; 128/898; 606/151, 153, 190, 219, 220, 1

[56] References Cited

U.S. PATENT DOCUMENTS

| | | |
|---|---|---|
| 4,304,236 | 12/1981 | Conta et al. |
| 4,319,576 | 3/1982 | Rothfuss ................ 227/179 |
| 4,379,457 | 4/1983 | Gravener et al. |
| 4,473,077 | 9/1984 | Noiles et al. ............. 227/179 |
| 4,476,863 | 10/1984 | Kanshin ................. 227/19 |
| 4,537,193 | 8/1985 | Tanner ................... 606/4 |
| 4,573,468 | 3/1986 | Conta et al. |
| 4,576,167 | 3/1986 | Noiles. |
| 4,603,693 | 8/1986 | Conta et al. |
| 4,646,745 | 3/1987 | Noiles. |
| 4,817,847 | 4/1989 | Redtenbacher et al. |
| 5,104,025 | 4/1992 | Main et al. .............. 227/179 |
| 5,108,420 | 4/1992 | Marks .................... 606/151 |
| 5,119,983 | 6/1992 | Green et al. ............. 227/179 |

FOREIGN PATENT DOCUMENTS

| | | |
|---|---|---|
| 3301713 | 7/1984 | Fed. Rep. of Germany ...... 606/153 |
| WO9006085 | 6/1990 | World Int. Prop. O. ............ 227/19 |

OTHER PUBLICATIONS

U.S. Surgical Corporation, "Auto Suture Information Booklet" 1990.
"Minimally Invasive Colon Resection (Laparoscopic Colectomy)", Jacobs et al., *Surgical Laparoscopy & Endoscopy*, vol. 1, No. 3, Sep. 1991, pp. 144–150.

*Primary Examiner*—Stephen C. Pellegrino
*Assistant Examiner*—Jeffrey A. Schmidt

[57] ABSTRACT

An apparatus for delivering a surgical device to a predetermined location within a tubular organ includes an elongated delivery member having a proximal and a distal end, a mounting mechanism for detachably mounting the surgical device at the distal end of the elongated delivery member and a releasing mechanism for releasing the surgical device from the mounting mechanism.

17 Claims, 6 Drawing Sheets

ANVIL DELIVERY SYSTEM

BACKGROUND OF THE INVENTION

1. Field of the Invention

This invention relates to a surgical delivery apparatus, and in particular, to an apparatus for delivering an anvil component to a remote location within a hollow organ to effect the joining of hollow organ sections by circular anastomosis.

2. Description of the Prior Art

Circular anastomosis is the surgical joining of separate hollow organ sections so that the sections intercommunicate. Typically, the anastomosis procedure follows surgery in which a diseased or defective section of hollow tissue is removed and the remaining end sections are to be joined. In accordance with such procedures, the operative tissue is exposed by making several extensive incisions in the body cavity wall and folding the cut tissue to provide access to the surgical site. The diseased section of the organ is removed thereby leaving two separate end sections of organ which are thereafter fastened by means of a stapling instrument which drives a circular array of staples through the end sections and simultaneously cores out any overlapping tissue to free the tubular passages.

Examples of such instruments for performing anastomosis of hollow organs are described in U.S. Pat. Nos. 4,304,236, 4,379,457, 4,573,468, 4,576,167, 4,603,693 and 4,646,745 all of which are incorporated herein by reference. In instruments of the types exemplified by these patents, opposed end portions of the organs to be stapled are clamped between an anvil component and a staple holding component, both of which are located at the distal end of the instrument. The clamped tissue is stapled by driving one or more staples from the staple holding component so that the ends of the staples pass through the tissue and are clinched by the anvil component.

In the typical application of joining first and second intestinal sections together, the operative tissue is accessed by forming at least one incision across the midline of the lower abdomen and folding the cut tissue to reveal the surgical site. The intestinal section in question is isolated and removed leaving the first and second intestinal end sections to be joined by anastomosis. The stapling instrument with mounted anvil component is applied to the operative site. Each end of the intestinal sections to be attached is then secured to their respective stapler or anvil component by a well-known purse string stitch to cause the tissue portions to tighten and to remain on the apparatus in position for permanent attachment by the staples. Thereafter, the anvil component is manually brought into close proximity to the staple holding component. The instrument is fired and the intestinal sections are attached by circular rows of staples or fasteners.

In some applications of the circular anastomosis technique, it is necessary to utilize a surgical instrument in which the anvil component is detachably mounted to the staple holding component. In such cases, the stapling instrument is introduced either surgically or transanally into the first intestinal section without the anvil component in place. The anvil component is subsequently surgically inserted within the second intestinal section. Both intestinal sections are secured to their respective anvil or stapler component by a drawstring. The anvil component is thereafter mounted within the staple holding component and the instrument is fired to complete the anastomosis. However, in such procedures the surgical site must be exposed by conventional surgical methods, i.e., incising of the lower section of the abdomen in order to emplace the anvil and join the tissue. This is undesirable in that it requires additional, often excessive time, causes additional trauma to the patient, and unnecessarily delays the anastomosis procedure. Further, it precludes the surgeon from using minimally invasive techniques to complete the anastomosis.

Therefore, in attaching first and second intestinal sections by circular anastomosis, it is highly desirable to prepare the intestinal sections and perform anastomosis using minimally invasive surgical techniques, particularly in situations which require the anvil component to be applied into an intestinal section independently from the stapling instrument. The present invention achieves this objective by providing a delivery system to be inserted transanally into the patient to deliver an anvil component through the intestine and to a targeted position therewithin. Thereafter, the intestinal sections can be laparoscopically severed to resect a defective or diseased tissue portion. The anvil component may be mounted within the staple holding component by laparoscopic means and the anastomosis completed.

SUMMARY OF THE INVENTION

The present invention provides a surgical apparatus for delivering an anvil component to a targeted section of a tubular organ so that anastomosis of two separated organ sections may be achieved using minimally invasive surgical techniques.

Generally stated, the apparatus includes an elongated delivery member, a mounting mechanism for detachably mounting the anvil component on a distal end of the elongated delivery member and releasing means for releasing the anvil component from the mounting means and into the targeted tubular organ section.

In a preferred embodiment, the surgical apparatus includes an elongated delivery member having a proximal and a distal end, a rod member extending coaxially within the elongated delivery member and having a bearing surface at its distal end and a mounting portion for detachably mounting the anvil component at the distal end of the elongated delivery member. The rod member is adapted for distal displacement relative to the elongated delivery member such that the bearing surface of the rod member engages the anvil component and causes release of the anvil component from the mounting portion and expels the anvil component into the targeted tissue section.

In an alternative embodiment, the anvil delivery system includes an elongated delivery member having a proximal and a distal end and a longitudinal bore extending therethrough and a hand grip portion disposed at the proximal end of the elongated delivery member to facilitate handling of the delivery system. The hand grip portion includes a longitudinal bore extending therethrough in axial alignment with the bore of the elongated delivery member. The system further includes a rod member extending coaxially within the longitudinal bores of the elongated delivery member and the hand grip portion. The rod member is adapted for longitudinal movement towards the distal end of the elongated delivery member. Preferably a proximal end portion of the rod member extends beyond a proximal end of the hand grip member. An anvil component is mounted at the distal end of the elongated delivery member.

In use, the distal end of the elongated delivery member with mounted anvil component is inserted within the hollow organ and advanced to a desired location in the tubular organ. A distal force is applied to the proximal end portion of the rod member, which causes the rod member to distally advance and engage the anvil component to effect release of the anvil component from its engagement with the elongated delivery member to expel the anvil component within the desired organ section.

The present invention also relates to a method for performing circular anastomosis of first and second intestinal sections using minimally invasive surgical techniques. The method comprises providing an anvil delivery system, including an elongated delivery member having a proximal and a distal end, mounting means for releasably mounting an anvil component to the distal end of the elongated delivery member and releasing means for releasing the anvil component from the mounting means to expel the anvil component within the targeted organ section. In accordance with the method, the distal end of the elongated delivery member with mounted anvil component is transanally inserted and advanced into the intestine until the anvil component is disposed beyond a diseased tissue section. The releasing means is thereafter actuated to release the anvil component from the mounting means and to place the anvil component within an intestinal section beyond the diseased section. The anvil delivery system is then withdrawn from the operative site.

Thereafter, a first and second side of the diseased tissue section is isolated and the diseased section is resected, preferably by laparoscopic means, leaving first and second intestinal sections having first and second stapled ends, respectively, with the anvil component disposed within the second intestinal section. An opening is made in the second stapled end of the second intestinal section so that the anvil component may be grasped and exposed. An apparatus for performing circular anastomosis of the first and second intestinal sections is introduced transanally and advanced into the first intestinal section until a distal end of the apparatus engages the first stapled end. An opening is made in the first stapled end to expose the staple holding component of the apparatus. The anvil shaft is then mounted within the staple holding component. This mounting interposes the two ends of the intestinal sections between the anvil component and the staple holding component. The apparatus is fired and the anastomosis of the first and second intestinal sections is completed. Thereafter, the apparatus is removed from the body.

DESCRIPTION OF THE PREFERRED EMBODIMENTS

Figure 1:
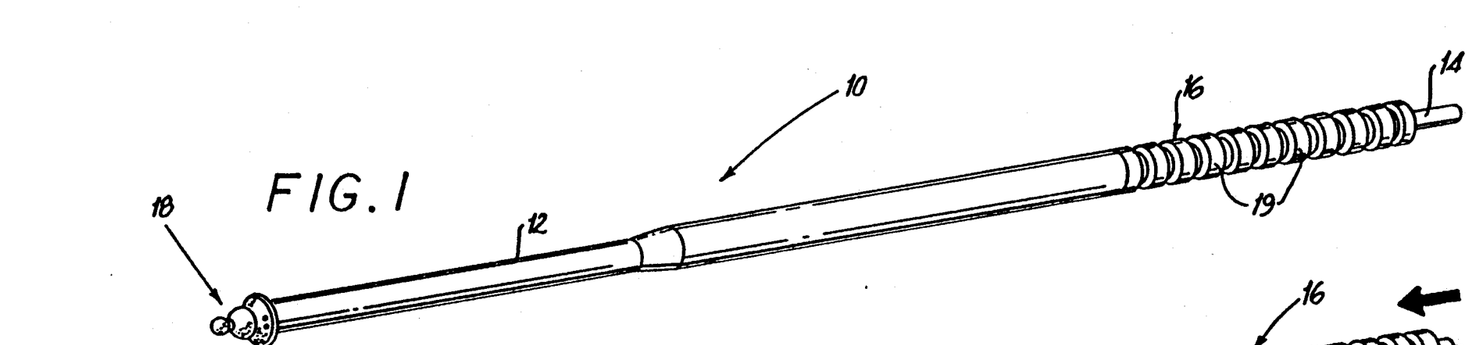
FIG. 1 is a perspective view of the anvil delivery system of the present invention.
Figure 2:
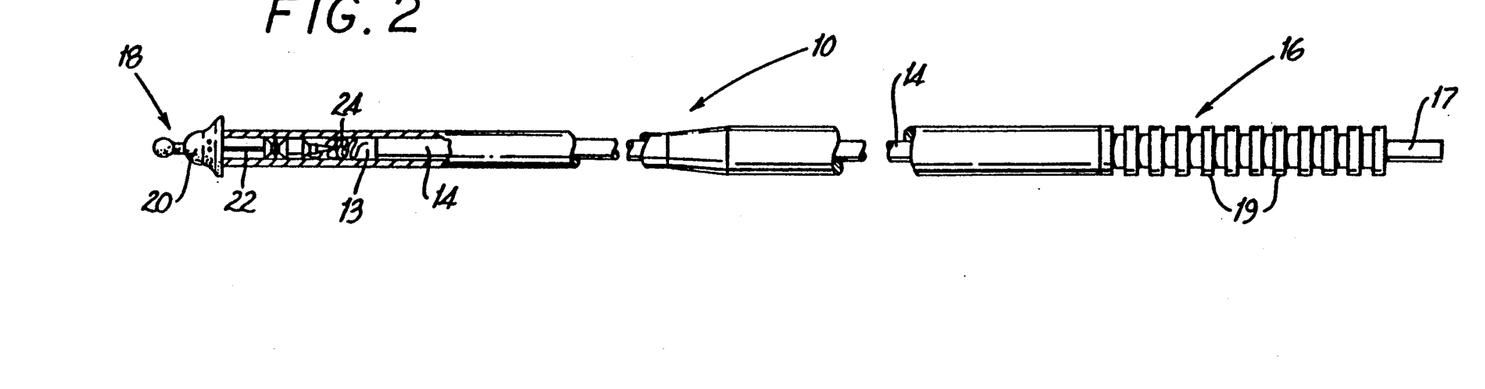
FIG. 2 is a side view of the delivery system of FIG. 1 with a partial cutaway of the distal end, illustrating the positioning of the anvil shaft of the anvil component and tail portion within the elongated sheath member when the apparatus is in the pre-fired condition.
Figure 3:
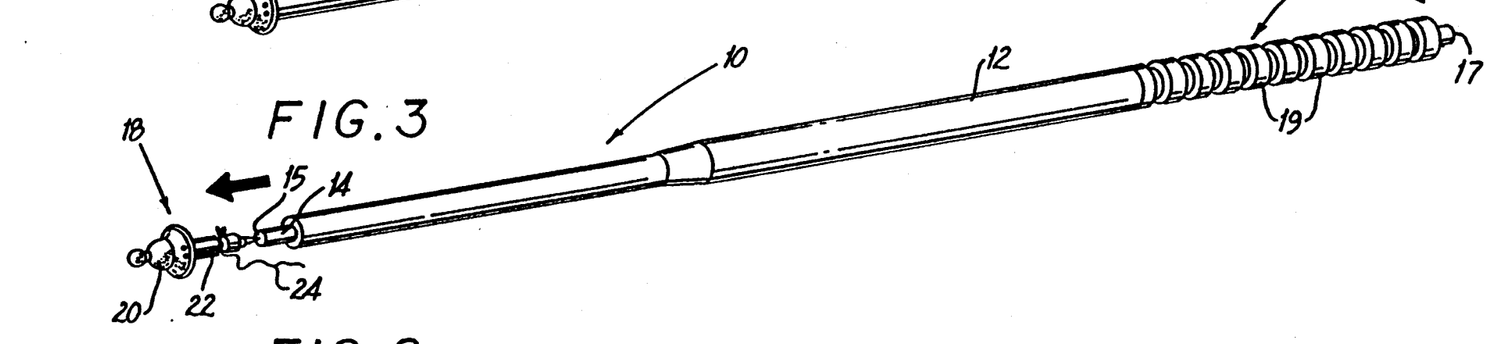
FIG. 3 is a perspective view of the delivery system of FIG. 1 in the post-fired condition with the anvil component expelled from the elongated sheath member.

Referring now to the drawings and, in particular, to FIGS. 1-3, there is shown an anvil delivery system in accordance with one embodiment of the present invention. Anvil delivery system 10 includes an elongated sheath member 12 having longitudinal bore 13 (see FIG. 2) extending therethrough, rod member 14, and hand grip member 16 disposed at the proximal end portion of sheath member 12. Hand grip member 16 also includes a longitudinal bore extending therethrough in axial alignment with longitudinal bore 13 of sheath member 12. In a preferred embodiment, hand grip member 16 includes a grip enhancing means such as a plurality of circumferential ribs 19 to facilitate grasping and maneuvering of the delivery system.

Anvil delivery system 10 expels anvil component 18 into a hollow tubular tissue section which is to be subsequently attached to an adjacent tissue section by circular anastomosis. Anvil component 18 includes anvil head 20 mounted on anvil shaft 22. Anvil shaft 22 is intended to be mounted within staple holding component 62 (see FIG. 8) of a stapling apparatus. Anvil head 20 may include an annular array of staple forming buckets to receive and bend staples fired from staple holding component 62. It is to be noted that the components of delivery system 10 can be modified to accommodate a variety of sizes and types of anvils.

Rod member 14 is slidably received within longitudinal bore 13 of sheath member 12 and the longitudinal bore of hand grip member 16, and is adapted to move in a distal direction relative to the remaining components in the delivery system. In a preferred embodiment, proximal end portion 17 of rod member 14 extends beyond the proximal end of hand grip member 16 as best shown in FIGS. 1 and 2. When a force is applied to proximal end portion 17, rod member 14 slides in a distal direction as shown by the arrow in FIG. 3. This distal movement causes bearing surface 15 of rod member 14 to engage shaft 22 of anvil component 18 and to release anvil component 18 from its engagement with elongated sheath member 12, and to expel the component into a targeted tissue section.

Anvil component 18 may be mounted to elongated sheath member 12 by conventional means. In a preferred embodiment and as best shown in FIG. 2, anvil shaft 22 is inserted within the distal end of sheath member 12 to mount the anvil component. Preferably, the diameter of shaft 22 is substantially equal to or slightly greater than the inner diameter of the proximal end of sheath member 12 such that the peripheral surface of shaft 22 frictionally engages the inner peripheral surface of sheath member 12 to assist in retaining anvil component 18 within the sheath member during insertion of the system within the tubular organ.

Delivery system 10 may range in length from about 60 cms to about 180 cms, however, any appropriate length may be chosen depending upon the particular application. In a preferred embodiment system 10 is straight, however, it is within the scope of the present invention for system 10 to be curved to facilitate placement of the instrument in particular body structures and to reach remote or relatively inaccessible operative sites. It is also possible for delivery system 10 to be flexible. Preferably all components of delivery system 10 are fabricated from polymeric materials, which thereby reduces the cost of manufacture of the system and makes it economically feasible to dispose the system after use.

Further understanding of the significant aspects of the delivery system of the present invention will become more readily apparent by the following description of the use of same. Referring now to FIGS. 4-10, the anvil delivery system 10 in accordance with the present invention is shown in a sequence of operation.

Figure 4:
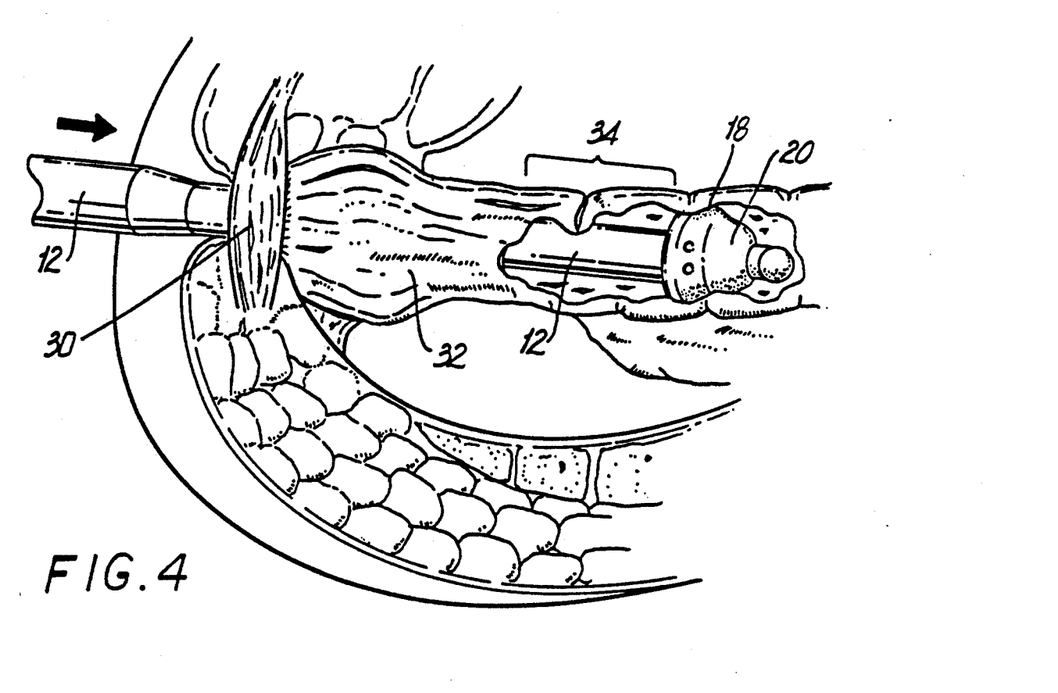
FIG. 4 is a perspective view of the delivery system of FIG. 1 inserted transanally and extending through a portion of the intestine.

Referring initially to FIG. 4, the surgeon grasps delivery system 10 by hand grip 16 and inserts the distal end of the system with mounted anvil component 18 through the rectal opening 30 and into colon or intestine 32. The system 10 is then advanced within intestine 32 until anvil head 20 extends slightly beyond diseased section 34 of the intestine.

Figure 5:
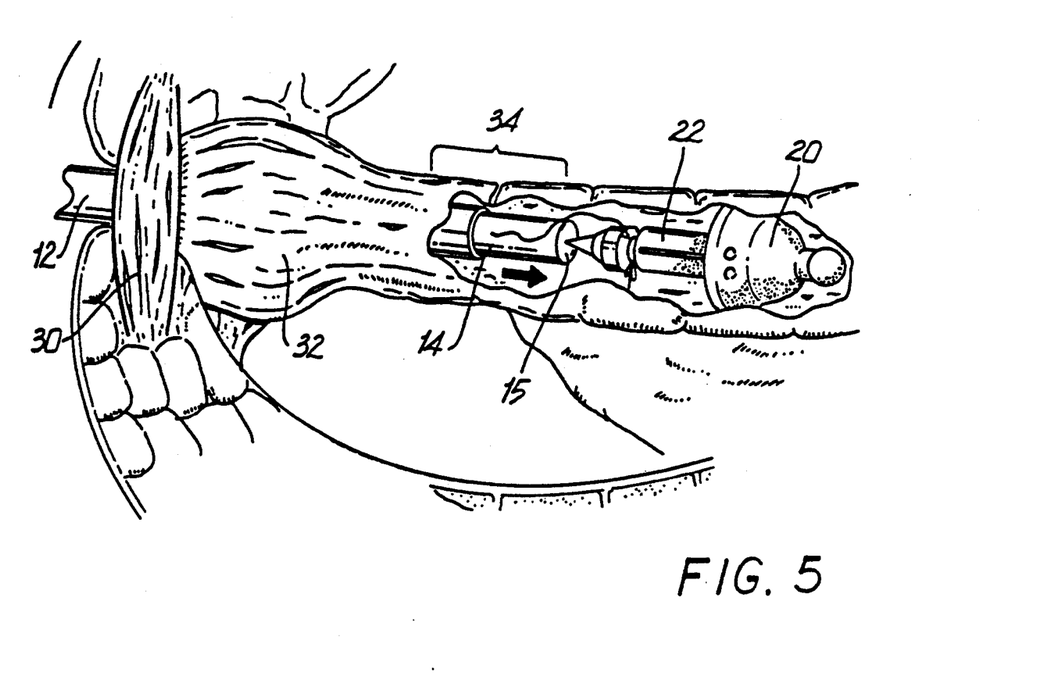
FIG. 5 is a perspective view of the delivery system of FIG. 1 inserted through the intestine and in the post-fired condition with the anvil component and tail portion expelled from the delivery system.

Referring now to FIG. 5, the delivery system is actuated by the surgeon by depressing proximal end portion 17 of rod member 14 (see FIGS. 1-3) to thereby effect distal movement of the rod member and cause bearing surface 15 of the rod member to engage the proximal end of shaft 22 and eject anvil component 18 into intestine 32. It is to be appreciated that after release from system 10, anvil component 18 is disposed in a section of intestine beyond diseased section 34. At this point in the procedure, delivery system 10 is removed from the colon.

The diseased tissue section is then excised followed by anastomosis of the adjacent severed tissue sections. Preferably, the remaining operative procedures will be performed using minimally invasive surgical techniques including laparoscopic means and instrumentation. This is a significant aspect of the present invention and is made possible by the prior transanal placement of the anvil component within the intestinal tissue. Such placement removes the need for incising the abdominal cavity to introduce the detached component to the operative site.

Figure 6:
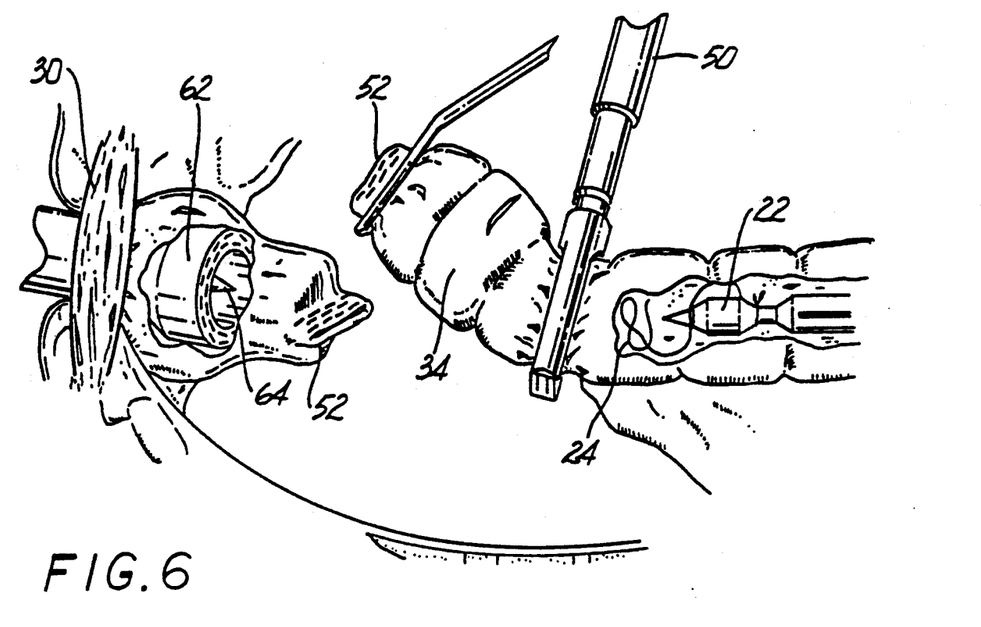
FIG. 6 is a perspective view illustrating removal of a diseased tissue section by a laparoscopic stapling instrument.

Referring now to FIG. 6, the preferred method for resecting diseased section 34 is illustrated. Through appropriate trocar sleeves, the surgeon applies a laparoscopic stapler 50 to both sides of diseased section 34. A suitable stapler for this purpose is described in commonly assigned U.S. Pat. No. 5,040,715 issued Aug. 20, 1991, the contents of which are incorporated herein. Each application of the stapler places two triple staggered rows of staples 52 while a knife cuts therebetween. FIG. 6 illustrates the staple rows after the application of stapler 50 to a section of the intestine nearest rectal opening 30. FIG. 6 also shows stapler 50 being applied to a section of the intestine beyond diseased section 34.

Figure 7:
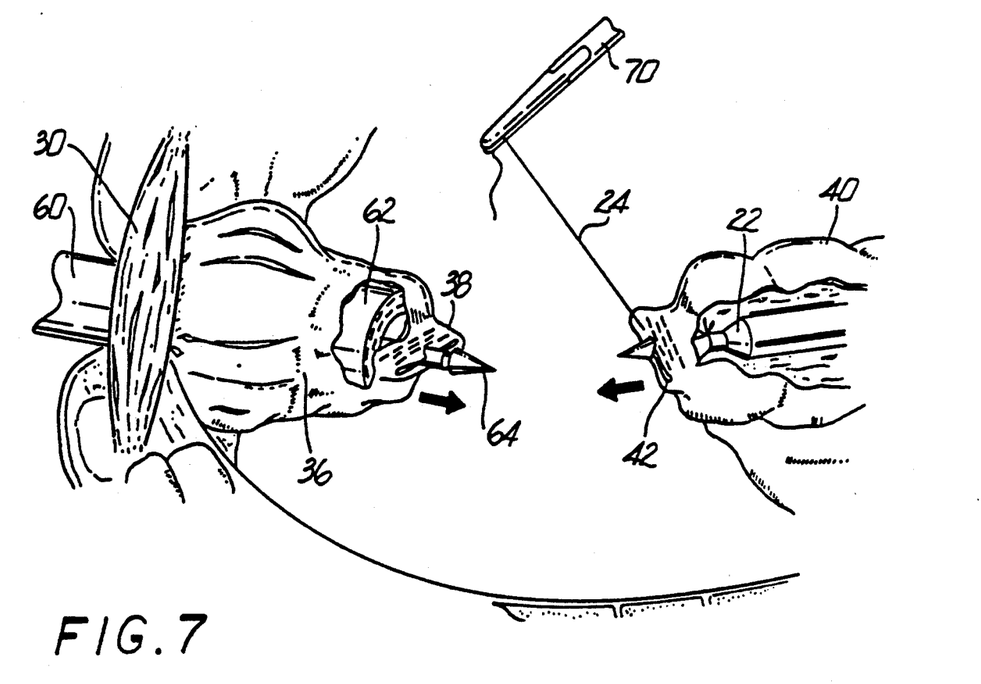
FIG. 7 is a perspective view after application of the laparoscopic stapling instrument, illustrating the formed first and second intestinal sections.

Referring now to FIG. 7, after application to both sides of diseased section 34, stapler 50 will have created two separated, closed end tissue sections 36, 40 having stapled ends 38, 42, respectively. This application will also have severed diseased section 34 from the remaining intestinal tissue. In FIG. 7, diseased section 34 is already removed from the operative site, preferably through one of the trocar sleeves (not shown). At this point in the procedure, anvil component 18 is positioned within tissue section 40.

Figure 11:
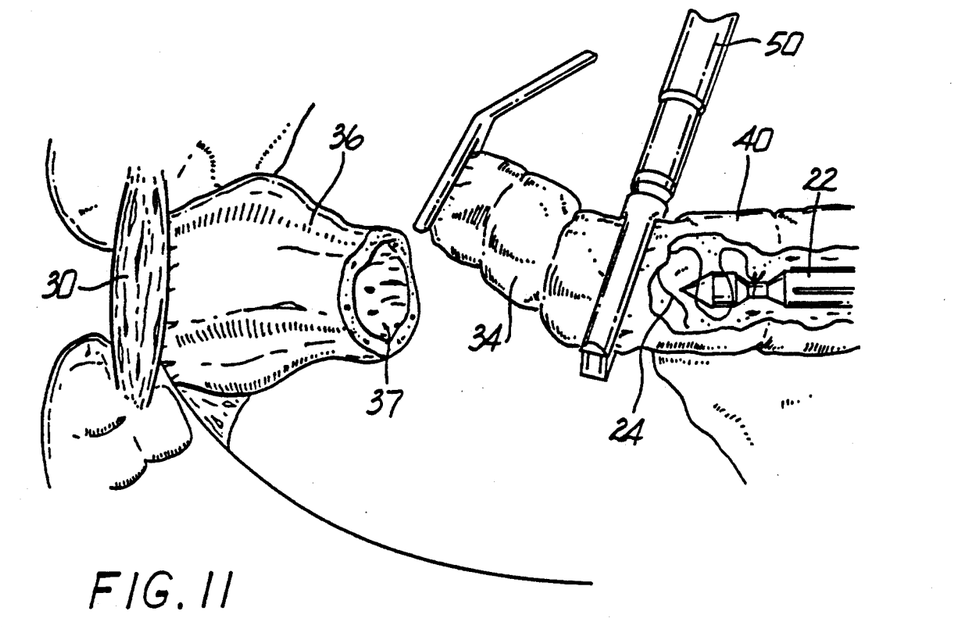
FIG. 11 is a perspective view illustrating an alternative method for resection and removal of the diseased tissue section in which the diseased section is to be removed through the rectal opening.
Figure 12:
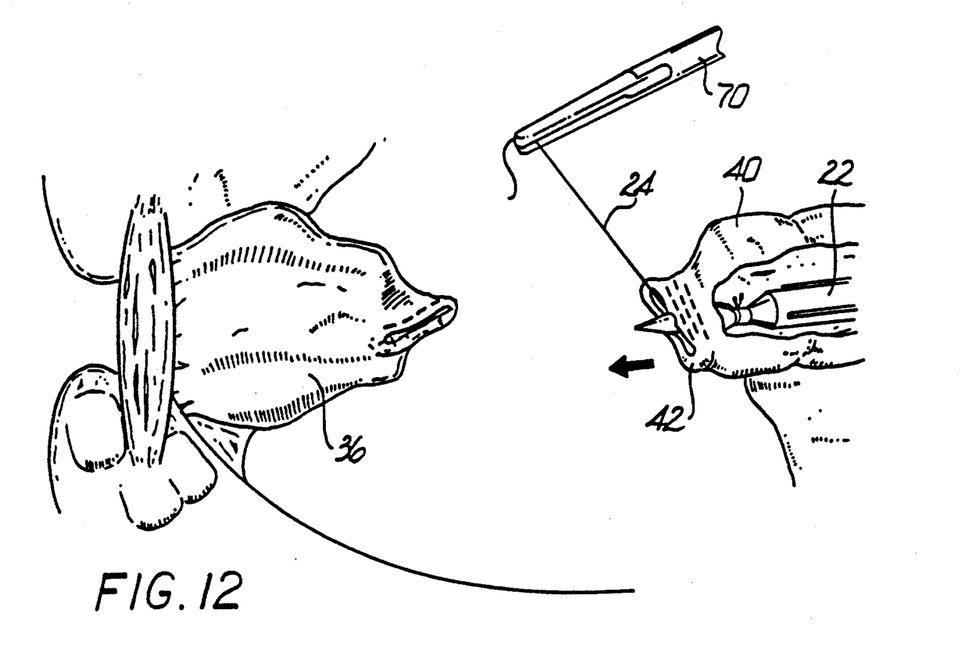
FIG. 12 is a perspective view after removal of the diseased section through the rectal opening and application of a laparoscopic stapling instrument to the first intestinal section.

Alternative laparoscopic instruments and methods may be incorporated to isolate diseased section 34 from the remaining intestinal tissue and to remove section 34 from the operative site. Referring to FIG. 11, the lower side of diseased section 34 may be severed from the intestinal tissue by, for example, a conventional scalpel. This step in the procedure creates intestinal section 36 having open end 37. Thereafter, stapling instrument 50 may be applied to the upper side of section 34 to close off and completely sever the diseased section from the intestine. Since the end of tissue section 36 is not closed, open end 37 provides an avenue to remove diseased section 34, i.e., removing the diseased section through the rectal opening 30. After removal, intestinal section 36 may be closed off as shown in FIG. 12 by conventional means, such as, for example, with a laparoscopic stapling instrument. Alternatively, tissue section 36 may be closed off around the staple holding component by a purse string suture.

It is also within the scope of the present invention to close off the upper side of diseased section 34 with a laparoscopic stapling instrument which fires a single row of staples, and then sever the diseased section on its upper side with a scalpel, laser or electrocautery device which is applied through a trocar sleeve. Thereafter, a similar cutting device may be used on the lower side of section 34 and the completely severed diseased section removed through end section 36 and out rectal opening 30 in the same manner as previously described. Intestinal section 36 may then be closed off with the stapling instrument. It is also possible to isolate diseased section 34 using a scalpel on both sides of the diseased section and to leave the ends of intestinal sections 36,40 open. Sections 36,40 may subsequently positioned for attachment by conventional drawstring or purse string sutures.

Referring to FIGS. 7-10 rejoining of the tissue ends is accomplished by inserting an apparatus 60 for performing circular surgical stapling of hollow tissue organs through rectal opening 30 and into intestinal section 36. Apparatus 60 includes staple holding component 62 with trocar 64 detachably mounted therewithin. Apparatus 60 may be any known instrument that is adapted to be inserted transanally to perform circular anastomosis of tissue sections. Examples of such instruments are described in commonly assigned U.S. Pat. No.

Figure 8:
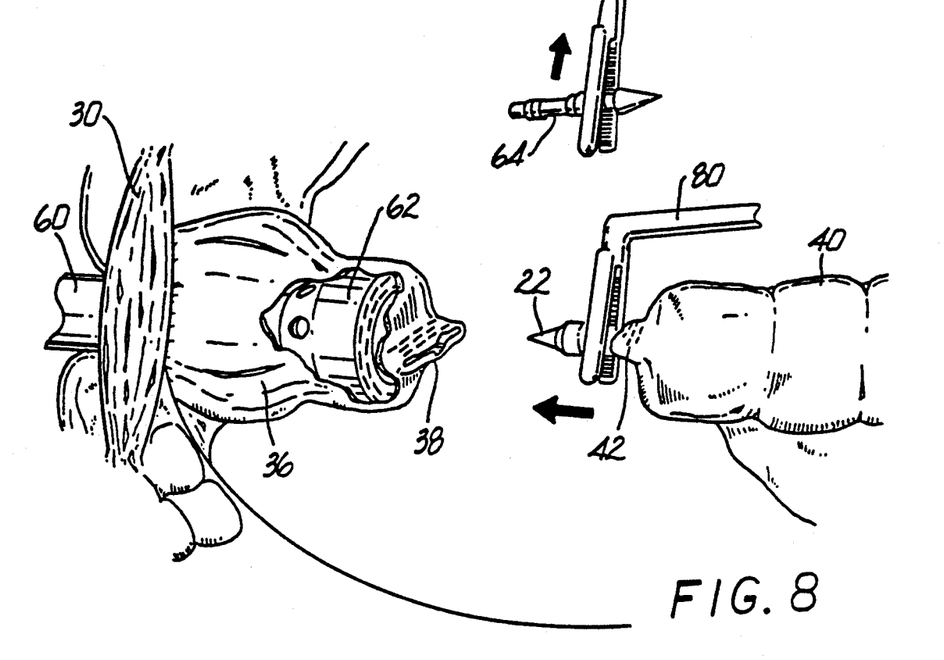
FIG. 8 is a perspective view with a partial cutaways of the first intestinal section, illustrating advancement of an apparatus for performing anastomosis and exposure of the anvil shaft from the second intestinal section.

4,304,236, 4,379,457, 4,573,468, 4,576,167, 4,603,693 and 4,646,745. Apparatus 60 is advanced into section 36 such that staple holding component 62 approaches stapled end 38 and trocar 64 contacts and penetrates the stapled end to form an incision through end 38 to expose the staple holding component. After the incision is formed in stapled end 38, the surgeon, through an appropriate trocar sleeve creates an opening with forceps or the like in stapled end 42 of intestinal section 40 and probes within the opening to locate and grasp anvil shaft 22. Preferably, the anvil assembly is provided with a tail 24 to assist in locating and removing the anvil assembly. Tail 24 is a section of thread or the like and is secured to shaft 22 prior to insertion of the delivery system to facilitate withdrawal of the shaft through the opening in stapled end 42. As shown, tail 24 is removed from the opening and pulled away from end 42 by forceps 70 until anvil shaft 22 becomes visible.

Referring to FIG. 8, trocar 64 is released from its engagement with staple holding component 62 and removed from the operative site through one of the trocar sleeves. Thereafter, the surgeon grasps anvil shaft 22 with grasping tool 80 and pulls the shaft until a portion of the shaft is exposed. At this point in the procedure, intestinal sections 36 and 40 are ready to be joined together by circular anastomosis. Intestinal sections 36, 40 are properly drawn over and secured around staple holding component 62 and anvil component 18, respectively, without maneuvering the tissue around these components. This is a significant feature of the present invention in that intestinal sections 36, 40 are secured in position for attachment without requiring the use of conventional drawstrings or purse string techniques to tighten the tissue sections around their respective stapler components.

Figure 9:
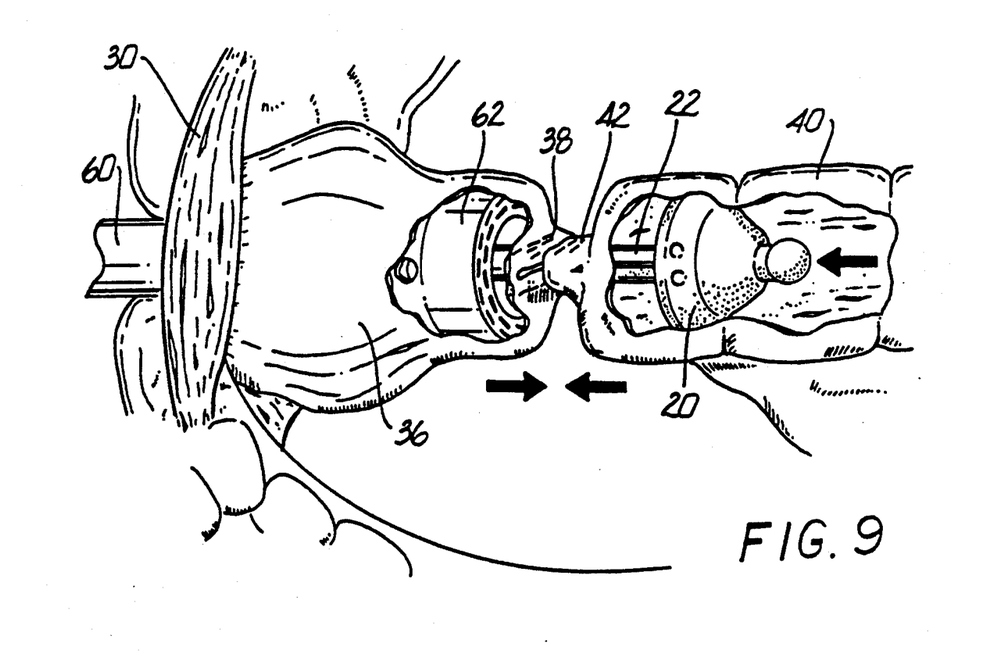
FIG. 9 is a perspective view with partial cutaways of the first and second intestinal sections, illustrating the anvil shaft of the anvil component mounted within the staple holding component.
Figure 10:
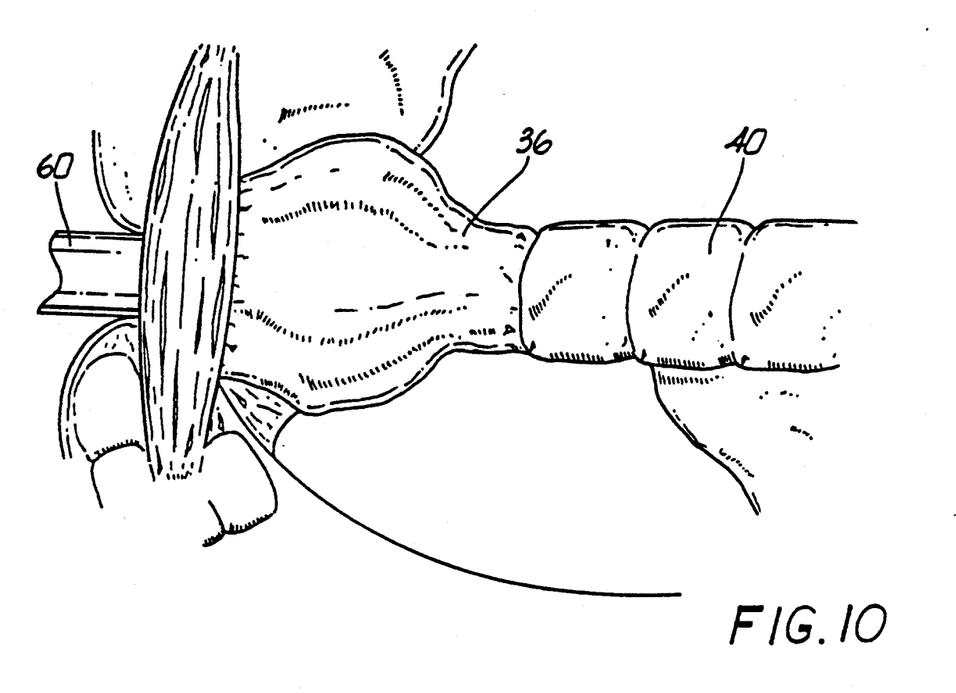
FIG. 10 is a perspective view of the anastomosis of the first and second intestinal sections after firing of the anastomosis apparatus.

Referring now to FIG. 9, through appropriate trocar sleeves, intestinal sections 36, 40 are approximated and anvil shaft 22 is mounted within staple component 62. This mounting properly interposes stapled ends 38, 42 of the intestinal sections 36, 40 between staple holding component 62 and anvil head 20, respectively. Thereafter, the stapling instrument is fired to perform the anastomosis. The excess portion of the ends of tissue portions are severed by the action of a knife edge incorporated in the anastomosis instrument. FIG 10 illustrates the anastomosis of intestinal sections 36, 40 after firing of the surgical apparatus. The surgeon thereafter removes the instrument with attached anvil component from the surgical site.

The present invention provides a novel device and method for delivery of an anvil component within a tubular organ which avoids the use of conventional surgery to expose the targeted tissue portion. The device can be manufactured cost-effectively and disposed of after use. The device makes it possible to perform anastomosis of hollow tissue sections entirely by laparoscopic techniques.

Although the present invention has been shown and described in terms of a preferred embodiment, it will be appreciated that various changes and other modifications are contemplated within the spirit and scope of the present invention as defined by the following claims.

I claim:

1. A surgical apparatus for delivery an anvil component within a tubular organ section, which comprises:
    an elongated delivery member dimensioned to be positioned within a hollow tubular organ, said elongated delivery member including a longitudinal bore extending therethrough and having proximal and distal end portions;
    an anvil component releasably mounted at said distal end portion of said elongated delivery member, said anvil component including an anvil shaft, said anvil shaft positioned within said longitudinal bore of said elongated delivery member and being dimensioned to form a frictional fit between an outer peripheral surface of said anvil shaft and an inner peripheral wall of said elongated delivery member to releasably mount said anvil component to said distal end portion of said elongated delivery member; and
    releasing means for releasing said anvil component from said distal end portion of said elongated delivery member.

2. The surgical apparatus of claim 1, wherein said releasing means comprises a rod member having proximal and distal end portions, said rod member received within said longitudinal bore of said elongated delivery member and being adapted for distal displacement relative to said elongated delivery member such that a bearing surface disposed at said distal end portion of said rod member engages said anvil component to effect distal displacement of said anvil component and release of said anvil component from said distal end portion of said elongated delivery member.

3. The surgical apparatus of claim 2, wherein said rod member and said elongated delivery member are flexible.

4. The surgical apparatus of claim 2, further comprising hand grip means attached to said proximal end of said elongated delivery member for facilitating insertion and removal of said elongated delivery member, said hand grip means having a longitudinal bore extending therethrough for reception of at least a portion of said rod member, said longitudinal bore of said hand grip means being in axial alignment with said longitudinal bore of said elongated delivery member.

5. The surgical apparatus of claim 4, wherein a proximal end portion of said rod member extends beyond a proximal end of said hand grip means.

6. The surgical apparatus of claim 4, wherein the length of the apparatus ranges from about 60 cms to about 180 cms.

7. The surgical apparatus of claim 4, wherein said hand grip means includes a plurality of circumferential ribs to assist in grasping and maneuvering said apparatus.

8. A method for performing circular anastomosis of first and second intestinal sections, which comprises the steps of:
    providing an anvil delivery system including an elongated delivery member having a proximal and a distal end, mounting means for detachably mounting an anvil component at said distal end of said elongated delivery member and releasing means for releasing the anvil component from said mounting means;
    mounting an anvil component at said distal end of said elongated delivery member, said anvil component having an anvil head and an anvil shaft;
    inserting said distal end of said elongated delivery member with the mounted anvil component through a rectal opening and advancing the delivery member through the intestine until the anvil component is beyond a diseased tissue section;

actuating said releasing means to release the anvil component from said mounting means;

withdrawing the anvil delivery system through the rectal opening;

laparoscopically isolating a first and second side of said diseased tissue section and excising said diseased tissue section, said isolating step forming first and second intestinal sections, said second intestinal section having said anvil component disposed therewithin;

securing said second intestinal section over said anvil head of said anvil component in position for attachment to said first intestinal section;

exposing said anvil shaft from said second intestinal section;

introducing an apparatus for performing circular anastomosis of said first and second intestinal sections into the rectal opening, said apparatus including a staple holding component at a distal end, said staple holding component adapted to receive and mount said anvil shaft therewithin;

advancing the apparatus into said first intestinal section;

securing said first intestinal section over said staple holding component in position for attachment to said second intestinal section;

mounting said anvil shaft within said staple holding component; and firing the apparatus to perform circular anastomosis of said first and second intestinal sections.

9. The method of claim 8, wherein said step of isolating said first and second sides of said diseased tissue section comprises laparoscopically stapling said first and second sides to form said first and second intestinal sections.

10. A method for performing circular anastomosis of first and second intestinal sections, which comprises the steps of:

providing an anvil delivery system including an elongated delivery member having a proximal and a distal end and a longitudinal bore extending therethrough, a hand grip portion disposed at said proximal end of said elongated delivery member to facilitate handling of the delivery system, said hand grip portion having a longitudinal bore extending therethrough in axial alignment with said longitudinal bore of said elongate delivery member, a rod member slidably received within said longitudinal bores of said elongated delivery member and said hand grip portion and adapted to move towards said distal end of said elongated delivery member, said rod member having a proximal end portion extending beyond a proximal end of said hand grip portion, and an anvil component mounted at said distal end of said elongated delivery member, said anvil component having an anvil head and anvil shaft, said anvil shaft inserted within said bore of said elongated delivery member at said distal end thereof to mount said anvil component to said elongated delivery member;

inserting said distal end of said elongated delivery member with said mounted anvil component through a rectal opening of a patient and advancing the delivery system through the intestine until said anvil component is adjacent a diseased tissue section;

applying a distal force to said proximal end portion of said rod member to distally displace said rod member such that a distal end of said rod member engages said anvil component to cause release of said anvil component from said elongated delivery member and placement of said anvil component into a portion of the intestine beyond the diseased tissue section;

withdrawing the anvil delivery system through said rectal opening;

laparoscopically isolating a first and second side of said diseased tissue section and removing said diseased tissue section, wherein said isolating step forms first and second intestinal sections having first and second stapled ends, respectively, said second intestinal section having said anvil component disposed therewithin;

accessing said anvil shaft of said anvil component to expose said anvil shaft from said second intestinal section;

introducing an apparatus for performing circular anastomosis of said first and second intestinal sections into the rectal opening, said apparatus including a staple holding component at a distal end, said staple holding component adapted to receive and mount said anvil component therewithin;

advancing the apparatus into said first intestinal section until said staple holding component engages said first stapled end;

accessing said staple holding component of the apparatus to expose said staple holding component from said first stapled end;

approximating said first and second intestinal sections;

mounting said anvil shaft within said staple holding component; and firing the apparatus to perform circular anastomosis of said first and second intestinal sections.

11. The method of claim 10, wherein said step of accessing said staple holding component of the apparatus comprises mounting a trocar within said staple holding component and advancing the apparatus into said first intestinal section until said trocar penetrates and forms an opening in said first stapled end.

12. The method of claim 10, wherein said step of mounting said anvil component within said staple holding component is performed using laparoscopic techniques and instrumentation.

13. The method of claim 10, wherein said step of accessing said anvil shaft includes making an opening in said second stapled end of said second intestinal section by laparoscopic techniques and instrumentation.

14. The method of claim 10, wherein said step of accessing said staple holding component includes making an opening in said first stapled end of said first intestinal section by laparoscopic techniques and instrumentation.

15. The method of claim 10, wherein said step of approximating said first and second intestinal sections is performed using laparoscopic techniques and instrumentation.

16. The method of claim 10, wherein said step of providing an anvil delivery system further includes securing a third portion to said anvil shaft of said anvil component.

17. The method of claim 16, wherein said step of accessing said anvil shaft comprises grasping said thread parts to expose a portion of said anvil shaft from said second intestinal section.

* * * * *